United States Patent [19]
Pennatto

[11] Patent Number: 5,360,596
[45] Date of Patent: Nov. 1, 1994

[54] PLUNGER HOMING MECHANISM FOR USE IN CHROMATOGRAPHY

[75] Inventor: Samson L. Pennatto, Danbury, Conn.

[73] Assignee: The Perkin-Elmer Corporation, Norwalk, Conn.

[21] Appl. No.: 504,826

[22] Filed: Apr. 5, 1990

[51] Int. Cl.⁵ .............................................. G01N 1/14
[52] U.S. Cl. ...................................... 422/63; 422/67; 422/81; 422/100; 422/104
[58] Field of Search ..................... 422/63, 67, 81, 100, 422/104, 64; 73/863.01, 864.21–864.24, 864.13, 864.16, 864.17

[56] References Cited

U.S. PATENT DOCUMENTS

| | | | |
|---|---|---|---|
| 3,915,651 | 10/1975 | Nishi | 73/864.16 |
| 4,199,013 | 4/1980 | Reich et al. | 222/135 |
| 4,325,909 | 4/1982 | Coulter et al. | 73/864.24 |
| 4,586,546 | 5/1986 | Mezei et al. | 422/100 |
| 4,713,974 | 12/1987 | Stone | 422/81 |

*Primary Examiner*—Timothy M. McMahon
*Attorney, Agent, or Firm*—Edwin T. Grimes; Thomas P. Murphy

[57] ABSTRACT

A plunger homing mechanism for use in automated chromatography. A plunger cap holder holds the plunger cap of a syringe within a housing. The housing is biased with an isolation spring within a casing. The casing is raised and lowered to move the syringe plunger held within the housing. When the casing is lowered and the plunger hits bottom, the relative movement between the housing and the casing is detected by a sensor. The casing movement is then caused to stop. This permits the detection of a home or reference position for the accurate and precise withdrawal of a sample to be analyzed. Additionally, damage to the syringe from over driving the plunger rod is prevented.

14 Claims, 3 Drawing Sheets

PLUNGER HOMING MECHANISM FOR USE IN CHROMATOGRAPHY

FIELD OF THE INVENTION

This invention relates generally to automated chromatography sampling and more particularly to an apparatus for determining and accurately positioning a syringe plunger in a home or reference position.

BACKGROUND OF THE INVENTION

In chromatography, samples to be analyzed are held in a sample vial having a rubber septum. To inject the sample held within the vial into a chromatograph for analysis, a syringe is used. The needle of the syringe is used to pierce the rubber septum. A sample is then withdrawn and subsequently injected into a chromatograph. Most often, this is an operation performed manually by a technician. This has proven to be inefficient and inaccurate, and not satisfactory for the standards of today.

Therefore, there have been attempts to automate this process. These attempts to automate the process have often resulted in complex mechanical systems. Chromatography inherently requires very accurate quantities of sample. These small, very precise quantities have been difficult to achieve in automated systems. Very accurate and reproducible control of the plunger is critical to chromatography, and is difficult to accomplish in an inexpensive automated system.

These difficulties have been compounded by the need to incorporate syringes that are not precisely manufactured into the automated system. The syringes, being relatively inexpensive, have manufacturing tolerances that vary. One of these variances is in the location of the plunger when it is fully depressed to the plunger stop prior to the withdrawing of the sample. Often, an automated plunger drive mechanism tends to overdrive the plunger stop, destroying the syringe.

Therefore, there is a need for a simple plunger homing mechanism that permits different syringes manufactured within a relatively large tolerance range to be inserted into an automated chromatography system, capable of accurately and reproducibly withdrawing a sample of a very precise volume from a sample vial.

SUMMAARY OF THE INVENTION

The present invention is directed to an apparatus for accurately positioning a syringe plunger in a reference or home position, stopped at the bottom of travel, before the taking of a sample to be analyzed in an automated chromatograph.

A plunger cap is removably placed into and held by a cap holder housing. A spring securely holds a plunger cap holder against the plunger cap and the cap holder housing. The housing is held within a casing. An isolation spring biases the cap holder housing within the casing but permits relative movement there between.

The plunger homing mechanism of the present invention is free to move with respect to a syringe body which is held by a syringe holder. A sensor detects relative movement between the housing and the casing. When relative movement is detected, the travel of the plunger homing mechanism is then stopped. This accurately positions the plunger of a syringe at the bottom of its travel prior to the withdrawing of a sample.

Accordingly, it is an object of the present invention to accurately position a plunger of a syringe at the bottom of its range of motion or stroke.

It is a further object of the present invention to withdraw a sample with repeatable accuracy.

It is an advantage of the present invention that syringes are prevented from breaking when the plunger reaches the bottom of its stroke.

It is a further advantage of the present invention that manufacturing variances in a syringe are accommodated without loss of accuracy.

It is a feature of the present invention that relative movement is detected between the casing and the cap holder housing.

It is a further feature of the present invention that it can be assembled easily.

These and other objects, advantages, and features will become more readily apparent in view of the following more detailed description.

DETAILED DESCRIPTION OF THE PREFERRED EMBODIMENT

Figure 1:
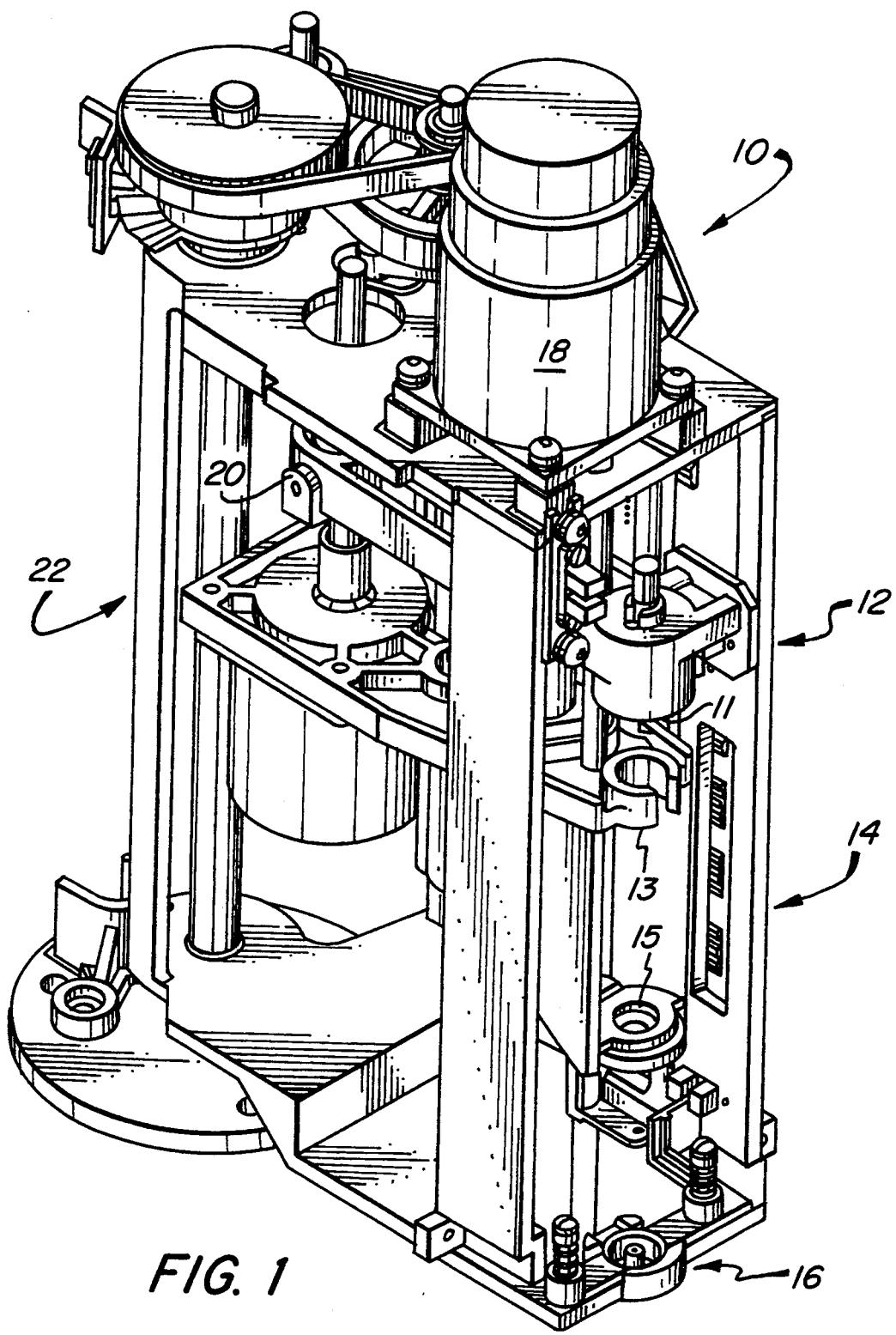
FIG. 1 is an isometric view of a device incorporating the present invention.

FIG. 1 illustrates a portion of an automated chromatograph incorporating the present invention. A tower assembly 10 is generally illustrated. The plunger homing mechanism 12 is held by a plunger carriage 20. The plunger carriage 20, and with it the plunger homing mechanism 12, is moved up and down by a lead screw motor assembly 22. A syringe body holder 14 is positioned directly below the plunger homing mechanism 12. The syringe body holder 14 is comprised of an upper syringe body holder 13 and a lower syringe body holder 15. The syringe body holder 14 is moved up and down by syringe motor assembly 18. The needle of a syringe extends through lower syringe body holder 15. When a syringe is inserted into syringe body holder 14, and the plunger cap of a syringe is inserted into the bottom portion 11 of the plunger homing mechanism 12, the assembly comprising the plunger homing mechanism 12 and syringe body holder 14 can be moved in unison to raise and lower the syringe without moving the plunger relative to the syringe body. In this way, the needle of the syringe can be lowered through guide 16 into a sample vial (not shown).

The plunger homing mechanism 12 of the present invention can readily be appreciated after a general understanding of the operation of an automated gas chromatograph. As shown in FIG. 1, the plunger homing mechanism 12 and the syringe body holder 14 can be moved up and down in unison if desired. This is done to move the syringe needle into and out of a sample vial or injector port without withdrawing or injecting a sample. The plunger homing mechanism 12 can also be moved independently of the syringe body holder 14 to accomplish the withdrawing or injecting of a sample. However, before the taking of a sample, the plunger must be positioned at tile bottom of its range of motion, or in a home or reference position. Therefore, when the plunger cap is raised, an accurate and precise sample can be taken.

Figure 2:
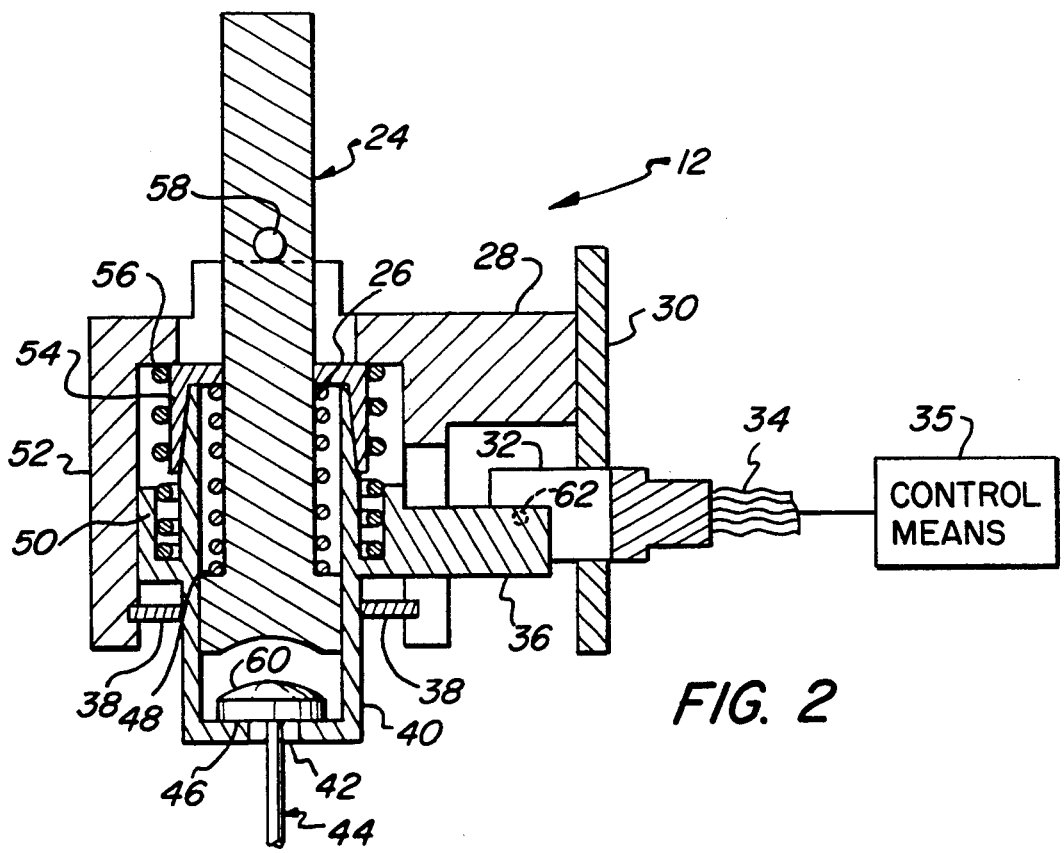
FIG. 2 is a cross section of the present invention illustrating the plunger cap holder in a raised position.

FIG. 2 more clearly illustrates the plunger homing mechanism 12 of the present invention. Referring to FIG. 2, a plunger cap holder 24 is biased downward by a plunger cap holder spring 26. The plunger cap holder 24 is contained in a cylindrical cap holder housing 40. The spring 26 is retained by a shoulder 48 at one end and a cap 54 at the other. Spring 26 forces plunger cap holder 24 downward into contact with a plunger cap 60. Plunger cap 60 rests on datum surface 46. The plunger rod 44 extends through a hole 42. The remainder of the syringe body is not shown for convenience of illustration. The plunger cap holder 24 can be held up for convenience of inserting a syringe by pin 58. When the plunger cap holder 24 is rotated 90 degrees, the pin 58 holds the plunger cap holder 24 in a raised position.

The cap holder housing 40 is held in a casing 52 by retaining ring 38. The housing 40 is biased downward away from the casing 52 by isolation spring 58. Retainer 50 retains the isolation spring 56, and retains the housing 40 within the easing 52. Attached to the casing 52 is a sensor arm 28. In turn, the sensor arm 28 is attached to a sensor bracket 30. A sensor holder 32 is attached to sensor bracket 30. Therefore, the sensor holder 32 is rigidly attached to the casing 52 and moves therewith. Attached to housing 40 is a sensor flag 36. The sensor flag 36 is isolated from the casing 52 by the isolation spring 56. The sensor flag 36 therefore moves with the housing 40.

The present invention, as configured, lends itself to easy manufacture and assembly. The housing 40, spring 26, cap 54, and plunger cap holder 24 can be made as a subassembly that is easily inserted into the casing 52 and retained by retaining ring 38.

Figure 3:
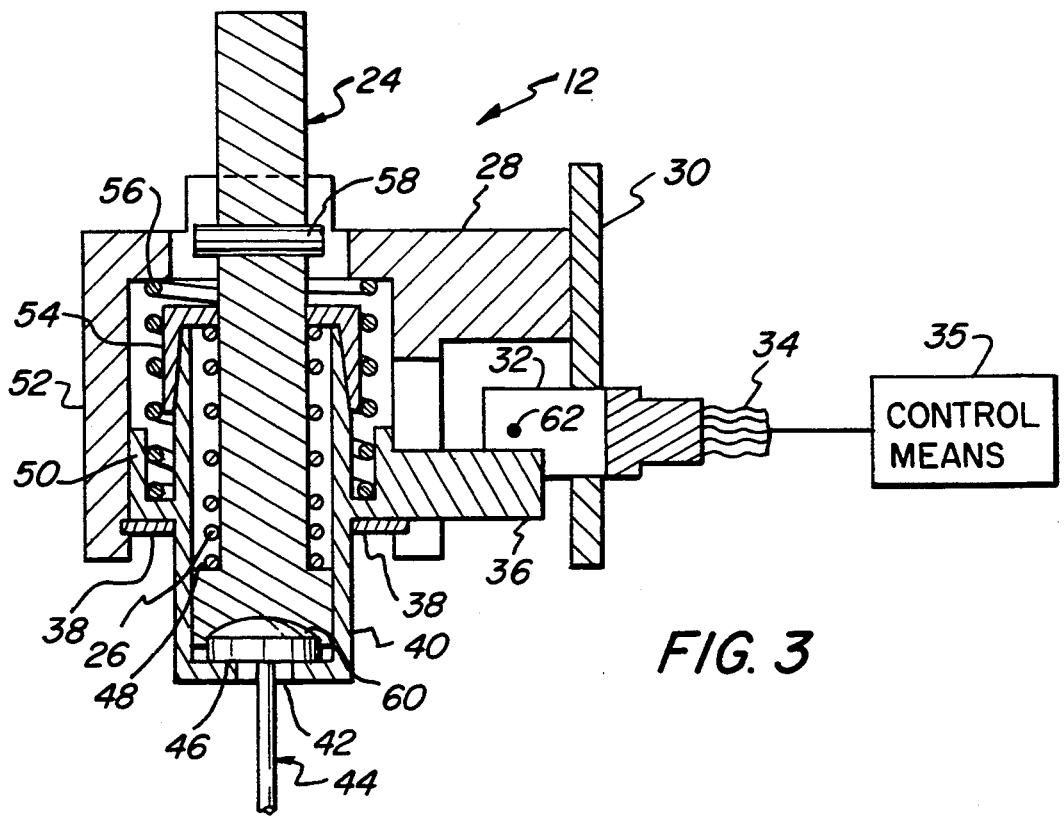
FIG. 3 is a cross section of the present invention illustrating the holding of a plunger cap in a position other than home.

FIG. 3 illustrates the plunger homing mechanism 12 after a syringe has been inserted and prior to the plunger of the syringe being positioned at the end of its travel, or home position. The isolation spring 56 biases the housing 40 into contact with retaining ring 38. Also, in FIG. 3 sensor 62 is not in a position to be triggered by flag 36.

Figure 4:
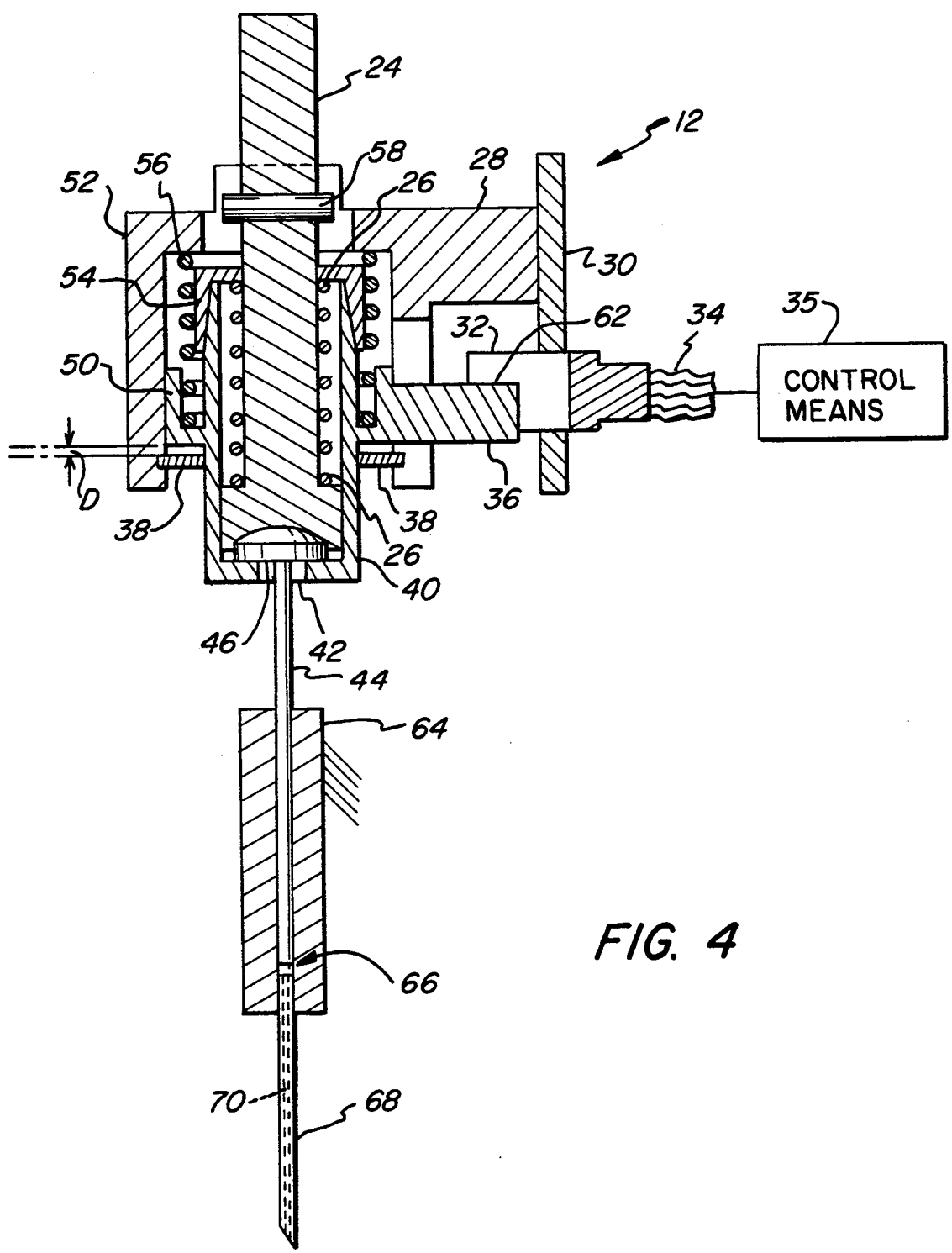
FIG. 4 is a cross section of the present invention illustrating the holding of a syringe cap in a home position.

FIG. 4 illustrates the plunger homing mechanism 12 after the plunger rod 44 has been depressed to the end of the plunger travel to the bottom or home position 66. In this position, the plunger rod 44 is fully depressed into the syringe body 64. With the position of the plunger rod 44 known a precise amount of sample can be withdrawn through needle bore 70 of needle 68. In this home position, the sensor 62 is triggered by flag 36 which causes the stopping of the downward motion of casing 52. The relative movement of housing 40 with respect to casing 52 can be seen by the gap between retaining ring 38 and retainer 50, labeled distance D. To accomplish this relative motion between the housing 40 and the casing 52, the spring 26 must be stiffer than time isolation spring 56. Therefore, the housing 40 will be pushed upward and not the plunger cap holder 24.

The operation of the device can now be readily understood with reference to the drawings. FIG. 3 illustrates the plunger homing mechanism 12 just after the insertion of a syringe. With the syringe body holder 14 holding the syringe body 64 stationary, the plunger homing mechanism 12 is lowered with respect to the syringe body 64. This moves the plunger rod 44 down until it contacts the bottom of the syringe or home position illustrated in FIG. 4. As the plunger homing mechanism 12 continues downward the plunger rod 44 will reach a point where it can move no longer. This is because it contacts the bottom of the syringe body 64 at position 66. This forces plunger cap 60 up against plunger cap holder 24. However, because spring 26 is stiffer than isolation spring 56, the entire housing 40 is moved upward. Flag 36, being attached to housing 40, is also moved upward relative to casing 52. The sensor 62 is thereby triggered by the upwardly moving flag 36. The triggering of sensor 62 causes the plunger homing mechanism 12 to stop its downward motion. Control means 35 are connected to sensor 62 by sensor cable 34. The control means 35 senses tile state of the sensor 62 and controls lead screw motor assembly 22. When the sensor 62 detects the flag 36 a signal is sent to the control means 35 to stop movement of the plunger homing mechanism 12. Therefore, the plunger homing mechanism 12 is prevented from unnecessarily loading the syringe plunger rod 44 after it has reached the fully depressed position. The preload of the plunger rod 44 and syringe body 64 can be adjusted by the distance D and by the spring constants of springs 26 and 56. The preload established by a distance D of 1/32th of an inch has proven to work well. Very accurate and precise samples can be taken with the use of this mechanism even though syringes may vary. Also, the syringes are not damaged due to over driving the plunger rod 44.

Although the preferred embodiment has been described and illustrated, it will be apparent to those skilled in the art that various modifications may be made without departing from the spirit and scope of this invention.

What is claimed is:

1. A syringe plunger homing apparatus comprising:
   a casing having a recess therein;
   a housing adapted to fit within said recess;
   a plunger cap holder adapted to slidably fit within said housing and hold a plunger cap;
   holder means for biasing said plunger cap holder into contact with said housing;
   an isolation spring biasing said housing away from said casing;
   retaining means, associated with said housing and said casing, for retaining said housing within said casing; and
   sensor means, associated with said housing and said casing, for detecting relative movement there between.

2. A syringe plunger homing apparatus as in claim 1 wherein:
   said holder means is a spring that is stiffer than said isolation spring, whereby said isolation spring compresses before said spring.

3. The syringe plunger homing apparatus as in claim 1, wherein said sensor means comprises:
   a mechanical switch.

4. A syringe plunger homing mechanism as in claim 1, wherein said sensor means comprises:
   a photo detector.

5. A syringe plunger homing apparatus as in claim 4, further comprising:
   a sensor holder adapted to accommodate said photo detector mounted on said casing; and
   a sensor flag mounted on said housing in a position capable of being detected by said photo detector.

6. A syringe plunger homing apparatus as in claim 5 wherein said photo detector and said sensor flag are adjusted to sense a predetermined movement of said housing relative to said casing.

7. A syringe plunger homing apparatus as in claim 6 wherein said predetermined movement comprises:
movement of 1/8th of an inch or less.

8. A syringe plunger homing apparatus as in claim 1, further comprising:
means for moving said casing relative to a syringe body.

9. A syringe homing apparatus for holding and positioning a syringe plunger as used in an automated chromatograph comprising:
a plunger carriage movable in a linear direction,
a casing mounted on said plunger carriage;
a housing adapted to hold a plunger cap positioned within said casing;
an isolation spring biasing said housing away from said casing;
a retaining ring holding said housing within said casing;
a first component of a sensor attached to said casing;
a second component of a sensor attached to said housing in a position to be detected when said housing moves relative to said casing; and
means for stopping relative movement between said casing and said housing when said first and second component of a sensor detect a relative movement between said casing and said housing.

10. A syringe homing apparatus as in claim 9 wherein:
said first and second sensors detect relative movement less than 1/8th of an inch.

11. A syringe homing apparatus as in claim 9 wherein said first and second component of a sensor comprise:
a photo detector and blocking flag.

12. A syringe plunger homing apparatus comprising:
a casing having a recess therein;
a housing adapted to fit within said recess;
a plunger cap holder adapted to slide within said housing and hold a plunger cap;
a holder spring biasing said plunger cap holder into contact with said housing;
an isolation spring biasing said housing away from said casing;
retaining means, associated with said housing and said casing, for retaining said housing within said casing;
sensor means, associated with said housing and said casing, for detecting relative movement there between; and
a syringe having a plunger and a plunger cap adapted to fit within said plunger homing apparatus.

13. A plunger homing apparatus for use in obtaining a precise sample for analysis as used in chromatography comprising:
a casing;
first motor means, attached to said casing, for linearly moving said casing up and down;
a housing adapted to fit within said casing and slide freely therein, said housing having an interior reference surface for mating with a plunger cap;
a first spring extending around said housing for biasing said housing away from said casing;
a retaining ring attached to said casing for retaining said housing within said casing;
a plunger cap holder extending through said casing and adapted to slide freely within said housing;
a second spring extending around said plunger cap holder for biasing said plunger cap holder against the reference surface;
locking means, attached to said plunger cap holder, for selectively locking said plunger cap holder in a raised position;
a syringe body holder;
second motor means, attached to said syringe body holder, for linearly moving said syringe body holder up and down;
control means, coupled to said first and second motor means, for controlling the relative linear movement of said casing and said syringe body holder; and
detector means, coupled to said casing and said housing, for detecting relative movement therebetween, whereby a syringe plunger can be positioned at the bottom of a syringe body without damaging the syringe and permitting an accurate and precise sample to be taken for analysis.

14. A plunger homing apparatus as in claim 13 wherein:
said second spring is stiffer than said first spring, whereby said first spring compresses before said second spring.

* * * * *